US009489736B2

(12) United States Patent
Lodron et al.

(10) Patent No.: US 9,489,736 B2
(45) Date of Patent: Nov. 8, 2016

(54) VISUALIZATION OF IMAGE TRANSFORMATION

(75) Inventors: Gerald Lodron, Gössendorf (AT); Marina Uray, Graz (AT); Heinz Mayer, Graz (AT); Peter Winkler, Graz (AT)

(73) Assignee: Joanneum Research Forschungsgesellschaft MBH, Graz (AT)

( * ) Notice: Subject to any disclaimer, the term of this patent is extended or adjusted under 35 U.S.C. 154(b) by 73 days.

(21) Appl. No.: 14/119,068

(22) PCT Filed: May 21, 2012

(86) PCT No.: PCT/EP2012/059331
§ 371 (c)(1),
(2), (4) Date: Nov. 20, 2013

(87) PCT Pub. No.: WO2012/160012
PCT Pub. Date: Nov. 29, 2012

(65) Prior Publication Data
US 2014/0125695 A1    May 8, 2014

(30) Foreign Application Priority Data

May 20, 2011 (EP) .................................... 11166971
Jun. 15, 2011 (EP) .................................... 11170026

(51) Int. Cl.
*G06T 7/00* (2006.01)
*G06T 11/00* (2006.01)
(Continued)

(52) U.S. Cl.
CPC ........... *G06T 7/0024* (2013.01); *G06T 11/001* (2013.01); *G06T 11/60* (2013.01); *A61B 6/032* (2013.01); *A61B 6/4085* (2013.01);
(Continued)

(58) Field of Classification Search
None
See application file for complete search history.

(56) References Cited

U.S. PATENT DOCUMENTS

2004/0184647 A1* 9/2004 Reeves et al. ........ G06T 3/0075
382/131
2006/0002630 A1* 1/2006 Fu et al. ....................... 382/294
(Continued)

OTHER PUBLICATIONS

Zhilkin et al., "3D image registration using a fast noniterative algorithm", Date: Sep. 2000, pp. 8 Source: http://citeseerx.ist.psu.edu/viewdoc/download?doi=10.1.1.26.1529&rep=rep1&type=pdf.*

(Continued)

*Primary Examiner* — Jwalant Amin
(74) *Attorney, Agent, or Firm* — BudzynFortunato IP Law, LLC

(57) ABSTRACT

A method is provided comprising: obtaining first and second datasets representative of first and second images of an object at different times, respectively; obtaining a deformation field, representative of changes between the first and second data sets, by performing a rigid or non-rigid registration; generating one or more masks and/or segmentations for selecting elements of the first image; selecting elements of the first image; transforming the first dataset using the deformation field to project the selected elements onto the second image; visualizing the deformation field or previously specified portions thereof; processing the deformation field or previously specified portions thereof to obtain data representative of different predetermined types of deformation; and visualizing the deformation field or one or more selected portions thereof, thereby to visualize the predetermined types of deformations separately and to enable a differentiation between changes in the patient and changes, in particular errors in the patient's position.

14 Claims, 5 Drawing Sheets

(51) Int. Cl.
G06T 11/60 (2006.01)
A61N 5/10 (2006.01)
A61B 6/03 (2006.01)
A61B 6/00 (2006.01)

(52) U.S. Cl.
CPC .............. *A61B 6/50* (2013.01); *A61N 5/1049* (2013.01); *G06T 2207/10081* (2013.01); *G06T 2207/10116* (2013.01); *G06T 2207/30096* (2013.01)

(56) References Cited

U.S. PATENT DOCUMENTS

| | | | |
|---|---|---|---|
| 2006/0267978 A1* | 11/2006 | Litke et al. | 345/419 |
| 2008/0037865 A1* | 2/2008 | Vetter et al. | 382/168 |
| 2009/0087124 A1 | 4/2009 | Nord et al. | |
| 2009/0129650 A1* | 5/2009 | Hawkes et al. | 382/131 |
| 2010/0061612 A1* | 3/2010 | Reisman et al. | 382/131 |
| 2010/0118648 A1* | 5/2010 | Zhao | G01V 1/44 367/35 |

OTHER PUBLICATIONS

Lester et al., "A survey of hierarchical non-linear medical image registration", Date: 2008, pp. 4 Source: https://cvit.iiit.ac.in/images/ConferencePapers/2008/Himanshu08Robust.pdf.*

Zhilkin et al., "Nonlinear registration of 3D images using patch algorithm", Date: 2002, pp. 1 Source: http://cds.ismrm.org/ismrm-2002/PDF9/2441.PDF.*

Arora et al., "Robust Image Registration with Illumination, Blur and Noise Variations for Super-Resolution", Date: 1999, pp. 21 Source: http://ac.els-cdn.com/S0031320398000958/1-s2.0-S0031320398000958-main.pdf?_tid=8120c36e-3956-11e6-9ef4-00000aab0f02&acdnat=1466695618_3cade9cd22faf2bb28c089849244bda5.*

Alan J. Lipton, "Local Application of Optic Flow to Analyse Rigid versus Non-Rigid Motion", Technical Reports, Jan. 1, 1999, pp. 1-13, Pittsburgh, PA.

Marc Tittgemeyer et al., "Visualising deformation fields computed by non-linear image registration", Computing and Visualization in Science, Jul. 1, 2002, vol. 5, No. 1., Germany.

Ferrant M. et al., "Real Time Stimulation and Visualization of Volumetric Brain Deformation for Image Guided Neurosurgery", Proceedings of Spie, The International Society for Engineering Spie, USA, Feb. 18, 2001, vol. 4319.

Stef Busking et al., "Direct Visualization of Deformation in Volumes", Computer Graphics Forum, Jun. 1, 2009, vol. 28, No. 3, pp. 799-806, The Netherlands.

Stef Busking et al., "Direct Visualization of Deformation in Volumes", Computer Graphic Forum, Jun. 1, 2009, vol. 28, No. 3, pp. 799-806, XP055030814, U.S.A.

Martin Von Siebenthal, "Anaylsis and Modelling of Respiratory Liver Motion using 4DMRI", MSc in Electrical Engineering and Information Technology, Jan. 1, 2008, pp. 1-157, XP055149429, http://e-collectionJibrary.ethz.ch/eserv/eth:30130/eth-30130-02.pdf, Zurich.

European Office Action of Nov. 4, 2014 relating to European Application No. 11 170 026.6.

* cited by examiner (a)

(b)

(c)

(d)

(a) (b)

(c) (d)

(e) (f)

(a)

(b)

(c)

(d)

(e)

(f)

VISUALIZATION OF IMAGE TRANSFORMATION

BACKGROUND OF THE INVENTION

Methods are known, for example irradiation therapy methods, which expose areas of a patient with doses of irradiation. Such therapy is usually preceded by an irradiation planning session in which the region and dosage of irradiation is determined. This may involve obtaining CT image data of the patient. These steps may be repeated to examine the progress of the therapy. To do this successive CT images of the patient are generated, compared and analysed. Problems that may arise in this process include movements of patient, patient respiration, and size changes of relevant portions of the patient, in particular the tissue to be treated or tissue that is not to be exposed.

WO 2009/042952 A1 describes an irradiation method using deformable image registration. The method includes obtaining a first image, obtaining a second image, determining a deformation field using the first and second images, and determining a transformation matrix from the deformation field. The transformation matrix may be used to position the patient relative to the radiation source to compensate for rotation and translation movements of the patient between the first and second images.

SUMMARY OF THE INVENTION

The present invention is defined in claim 1. Features of preferred embodiments are recited by the dependent claims.

DETAILED DESCRIPTION OF THE DRAWINGS

Introduction

Figure 1:
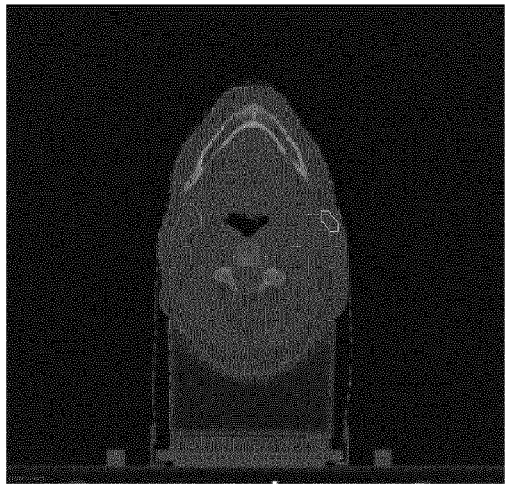
FIG. 1 illustrates a CT data set from the planning state, (a) and (c) with 3 superimposed structures (salivary glands and irradiation or tumour region) visualized as coloured contours and surfaces. (b) and (d) illustrate the superimposed dosage resulting from the planning shown as colour encoded image (b) and with colour encoded isocontours (d).
Figure 1:
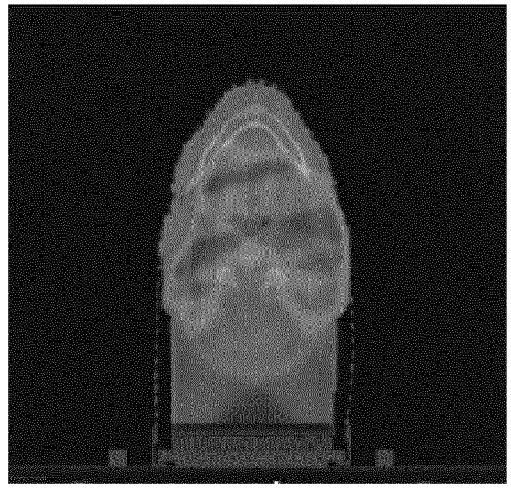
Figure 1:
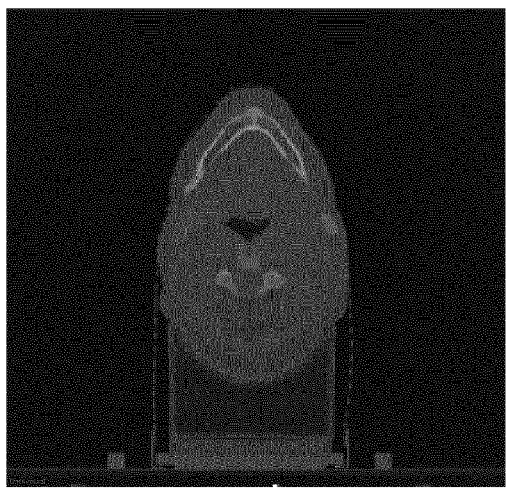
Figure 1:
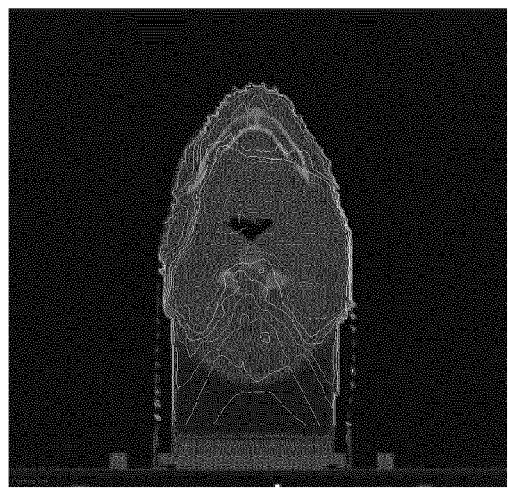

Morphologic changes during radio oncological therapy cause changes in the dosage distribution as compared to the dosage distribution at the time of the initial radiotherapy planning. Such changes are quantified by applying the original irradiation plan onto data sets (e.g. CT or MRT images) that are obtained at a later stage. For this purpose the contours are applied by means of non-rigid image registration.

The morphology of the irradiated volume is exposed to various influences during the course of a series of treatments: shrinking or swelling of tissue, curvatures and torsions due to incorrect positioning or support of the patient. However, the choice of adequate corrective measures in adaptive radiotherapy (ART) requires knowledge of the type and magnitude of these sources of error.

Accordingly, in an embodiment the invention takes into account changes in the dosage distribution in the target volume and organs at risk, and static parameters in transformation matrixes in order to better judge the type of transformation and to make better predictions of dosimetric changes.

In particular, in an embodiment of the invention there is provided a software-implemented method for non-rigid image registration of CT data in selected regions of a patient, e.g. the ENT region. The method comprises calculation of transformation vectors representing translation and deformation of tissue between different data sets (CT images).

The transformation matrixes obtained by non-rigid registration of CT-based data sets are used to adapt the planning contours, parameterized and statistically evaluated. After applying the original irradiation plan onto the subsequent CT, the correlation of morphologic changes and dosage changes can be analyzed. Besides diverse statistical parameters the basis for an appropriate assessment of the data by an expert is the visualization of the deformation itself. Several representations of the deformation field and the transformed data support the interpretation of the modifications of the body.

In order to evaluate morphologic changes, voxel data of the transformation vector field preferably undergoes filtering (e.g. band pass, smoothing, etc.) and statistical processing, e.g. on the basis of mean values, standard deviations and vector lengths. In particular, morphologic changes, represented by mean vector lengths in filtered transformation vector fields, may be correlated with dosimetric changes. The transformation matrixes enable a visualisation of deformations of the entire scan volume (position inaccuracies) by using global filters or a visualisation of local size reduction and deformation processes by using local filters.

Thus, it is possible to analyze morphologic changes during a series of irradiation treatments and to non-rigidly register contours onto a current CT dataset. Thereby ART can be assisted, i.e. the adaptation of the irradiation and optimisation of the dosage plan in response to changes in the shape and position of the irradiated volume. Thus, the analysis of the deformation as result of the non-rigid registration enables a specific correction depending on the nature of the morphologic changes.

DESCRIPTION OF A PREFERRED EMBODIMENT

In an embodiment of the present invention there is provided a software-implementable method for improving the workflow and therapy in the field of irradiation-based tumour treatment. As in conventional systems, the method comprises generating CT images of patients to be treated, and planning the treatment on the basis of such images. The planning maybe manual, semi-automatic or automatic and involves the marking of regions of interest in the CT images (e.g. the tumour region, salivary gland etc. See FIG. 1). Thereby the irradiation system can be aligned in order to directly irradiate the tumour without undue exposure of important organs such as the salivary gland. The irradiation is then performed over a period of weeks or even months in successive sessions, wherein the anatomy of the patient may change (patients may lose weight; organs change their size and position; patients have different positions; etc.). Since a new planning (drawing of contours) can be difficult and time consuming, this is to be avoided unless there are significant changes in the patient's anatomy. This may result in inaccurate irradiation.

The present invention aims to provide a tool to distinguish between a change in position and an actual deformation. Thereby, unnecessary re-planning steps can be avoided, because change in a patient's positioning can be addressed by re-positioning the patient, whereas only actual deformations require a re-planning.

According to an embodiment of the present invention, a new dataset (usually CT image) is generated at regular intervals. By comparing a chronological staggered CT image(s) with the original CT image on which the planning was based, the planning contours can be automatically adapted to the current data set. By detecting the necessity of a re-planning, the accuracy of the irradiation can be optimised, resulting in higher chances of successfully treating the patient.

In addition, other data such as dosage distribution (e.g. to what dosage has the salivary gland been exposed, see also FIG. 1b) can be transformed onto more recent CT data. Thereby, the sum of dosage data of each irradiation session becomes more accurate.

When comparing the planning CT with the current CT, a so-called non-rigid registration is performed. Thereby, a deformation (vector) field is generated that deforms the planning CT so as to substantially obtain the current CT. Using the deformation field, the contours and/or dosage is transformed and applied to the new (current) data set.

Subsequently, instead of discarding the deformation field as usually done, it is visualised in order to display the position, magnitude and quality of changes. For this purpose the rigid portion of the deformation field (i.e. the portion associated with rotations and translations) is not displayed, as this does not contain any information that is sought at this stage. (Such information may reflect an inaccurate positioning of the patient, which may be useful at some other stage. However, in terms of evaluating the therapy, only the non-rigid portion is relevant).

Figure 2:
FIG. 2 illustrates different visualisation possibilities of a deformation field, (a) with a colour encoded image representing the absolute value (magnitude or amplitude) of the 3D vectors on current CT plane overlaid with global transparency on the original CT data set. (b) is the colour encoded isocontour representation of (a) without transparency. (c) and (d) are 2D projections of some 3D deformation vectors of current CT plane onto its plane wherein resulting 2D vectors are displayed as (c) lines and (d) as amplitude dependent magnified arrows. Also the colour in (c) and (d) refers to the local 3D deformation magnitude. Subfigure (e) is like (c) but shows only local transparency and (f) displays (e) as colour encoded image.
Figure 2:
Figure 2:
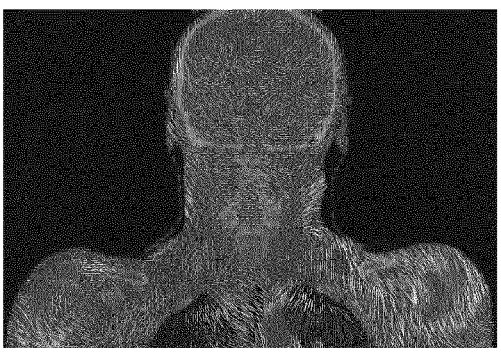
Figure 2:
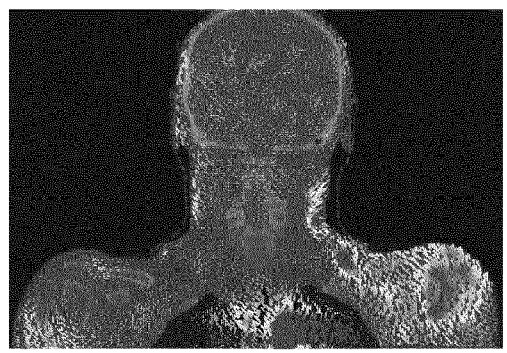
Figure 2:
Figure 2:
Figure 3:
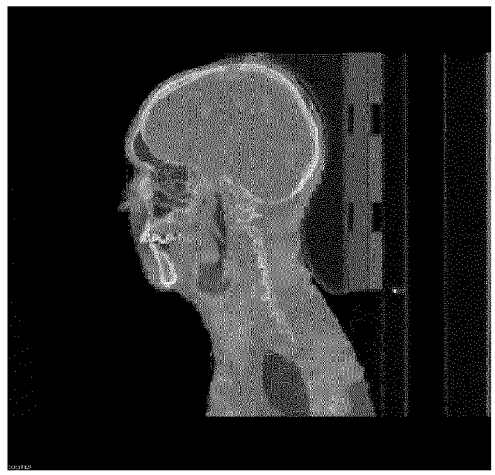
FIG. 3 illustrates a sagittal visualization of a deformation field overlaid on the CT data set (a) with global opacity and (b) with transparency of small magnitudes. (c) and (d) represents a filtered deformation field wherein (c) only show deformations of structures smaller scale without "distracting" coarse ones. (d) displays this coarse filtered deformation caused by errors in patient-positioning (neck curvature change). Globally these visualizations can be interpreted as a change of the oesophagus and a patient positioning error. (e) and (f) illustrates a 3D visualization of the deformation on the planes whereby (f) is zoomed.
Figure 3:
Figure 3:
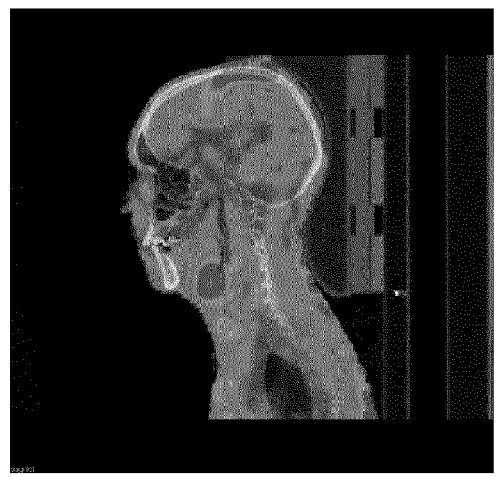
Figure 3:
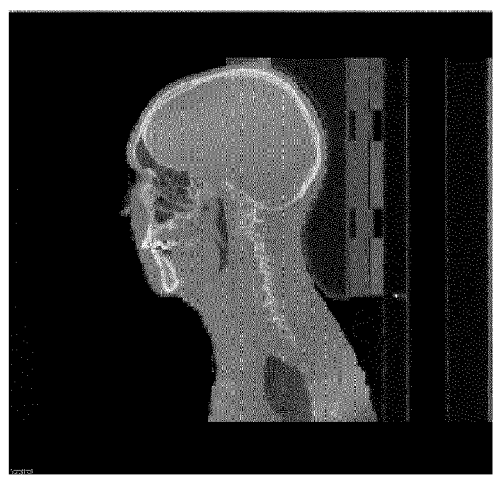
Figure 3:
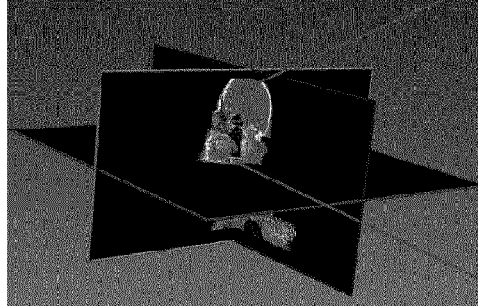
Figure 3:
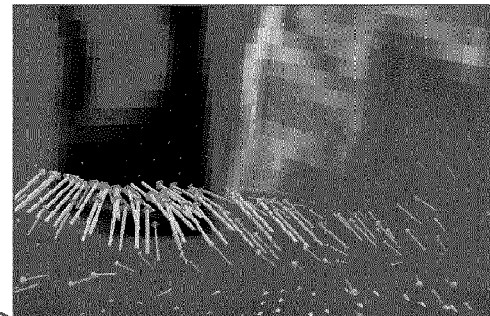

Different methods may be used to visualize the vectors of the deformation field. In the present case, the deformation fields represent 3D vectors. As it is preferred to display 2D sections of CT datasets, the 3D vector datasets are intersected with a 2D plane (axial, coronal, saggital, oblique), thereby generating a 2D matrix/image containing 3D vectors (see FIGS. 3e and f). However, it is preferred not to display these 3D vectors. Instead, in embodiments of the invention three alternative visualisation methods are implemented:

1. Absolute value (magnitude) of the 3D deformation vectors (see FIG. 2a)
2. Colour-coded isocontours of 1.
3. Projections of the 3D vectors onto the 2D intersection place (resulting in 2D vectors) and simultaneous colour-coding by means of the new 2D magnitude or original 3D vector magnitude. Also the thickness of the arrowhead of the drawn vectors (not only the length) can be changed due to their magnitude. Preferably, only a fraction of the vectors is displayed (e.g. every $x^{th}$ vector), see FIG. 2b).

For physicians it is important to be able to distinguish between different kinds of deformations, e.g. has a patient been badly positioned by the physician (e.g. different neck curvature in different CT images), has an organ moved or has it changed its size. This is hardly visible from raw deformation fields. Accordingly, in an embodiment of the present invention, filtering in accordance with the strength (deformation magnitude, see FIG. 3b) and/or the scale (object/structure deformation's spatial size, see FIGS. 3c and d) of the deformations is performed. Thereby, it is possible to selectively display different types of changes e.g. "strong" movements (e.g. shoulder movements) or minor movements (e.g. organ changes).

The deformation strength (small and large deformations) and scale (coarse and fine structures) can be adjusted separately e.g. across continuous intervals (minimum and maximum strength and scale), i.e. to display only deformations of objects at the size of a specific organ. In this case it is possible to filter in accordance with the interesting organ and with interesting amplitudes (e.g. position errors and small vector lengths <1 mm are currently uninteresting and undesired in visualization).

Figure 4:
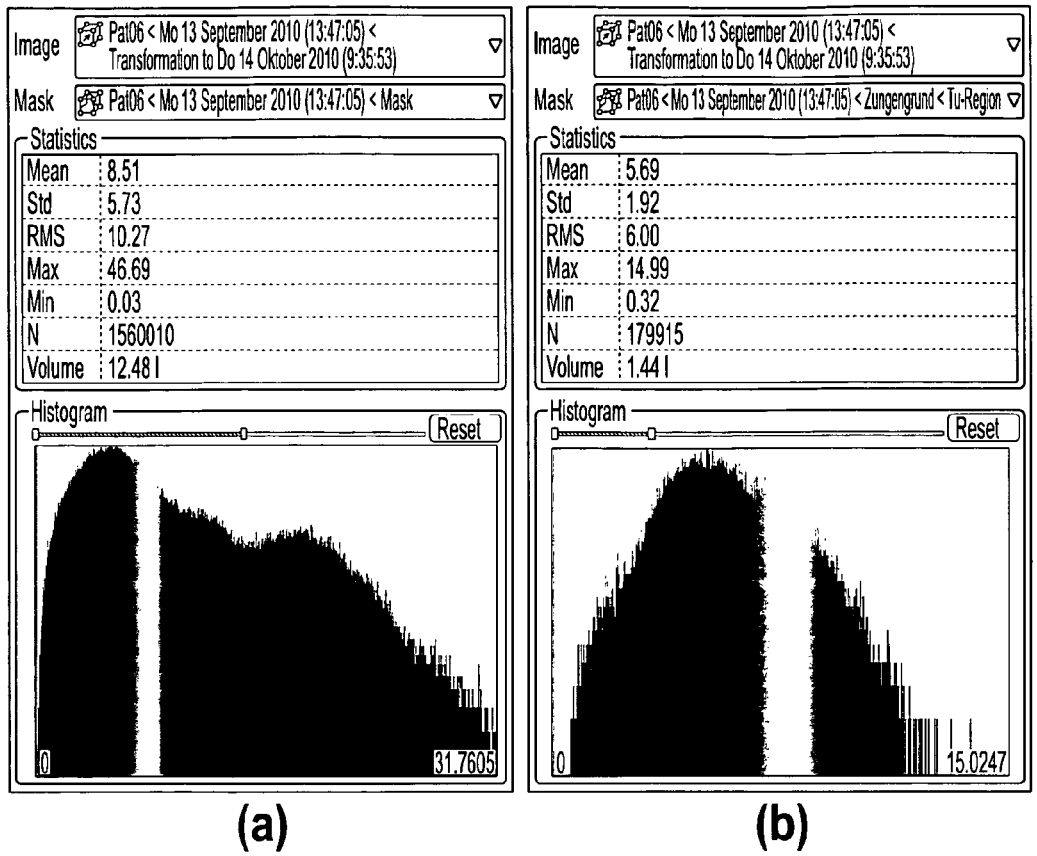
FIG. 4 illustrates a statistical evaluation of the deformation field with common statistical parameters like mean, standard deviation, root mean square, etc. Additionally the colour coded histogram of the deformation magnitude is painted wherein (a) refers to the entire patient and (b) to the irradiation (tumour) region. Globally the number of small deformations is larger than the number of large deformations; in the tumour region the changes have a mean value of 5.69 mm. (c) shows the volume change of different regions.
Figure 4:
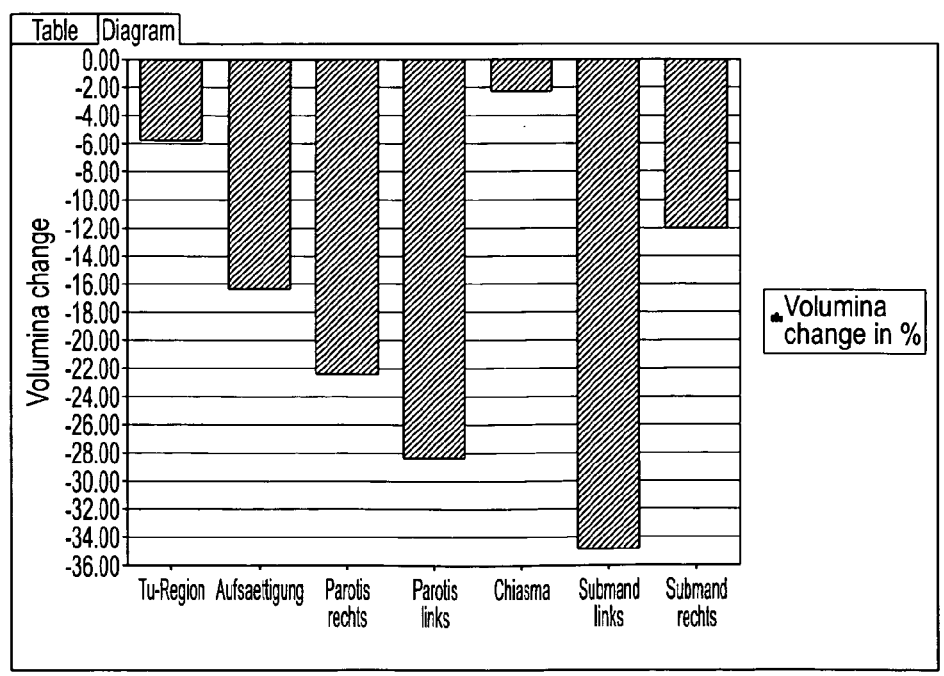

According to an embodiment of the invention, the planning CT is transformed by means of the filtered deformation field. This is done iteratively on the basis of different deformation scales. Thereby a "3D video" may be generated in which initially coarse spatial structure changes are displayed (neck movements, see FIG. 3b), followed by fine spatial structure movements (organ movements, see FIG. 3a). Thus, the video successively displays different kinds of changes wherein the time axis represents the scale or size of moving/deforming organs Also, in an embodiment of the invention, a histogram of the deformation vectors is displayed (see FIG. 4a), and to restrict this to a selected region (e.g. a tumour region, see FIG. 4b).

According to an embodiment of the invention, inverse mapping is employed in order to transform volume data (such as contours). That is, vectors are calculated that point from the current data set to the original data set. This may be done through image registration. However, for the purposes of visualisation it may be more intuitive to display vectors that point from the original dataset to the target (current) dataset. This may be done over a second registration, per vector field inversion or by registration algorithms which generate the forward and the inverse deformation field simultaneously. This forward deformation field can also be used to transform continuous point data instead of volume data. To eliminate rigid content from the non-rigid transformation field (for visualization) it is also possible to make a rigid registration step before the non-rigid registration itself. This way, point data can be transformed while both deformation fields can be visualized.

It may be required that the volume data represent arrays of 2D polygons that reside in the same spatial plane as the CT data. For this reason a suitable transformation may be undesirably complicated (e.g. transformed polygons are no longer in the same spatial plane as the z-axis, i.e. new polygons must be generated). To address this, in an embodiment of the invention, a new volume is generated from the 2D curves, and the new volume is transformed and intersected with the resulting new planes. In addition, image processing steps to smoothen frayed regions may be applied.

In accordance with an embodiment of the invention, the method comprises determining a forward deformation field, a transformation matrix, and an inverse deformation field. The forward and inverse deformation fields are processed to eliminate a rigid portion thereof attributable to rotation and/or translation of the object (patient).

In particular, first a segmentation of $1^{st}$ and $2^{nd}$ CT images is made to obtain two input images and two binary segmentation images. From these four images the transformation matrix (4×4 matrix containing translation and rotation) is determined. With the transformation matrix, the two input images and the two segmentation images, the forward deformation field and the inverse deformation field are determined.

More particularly, first the transformation matrix is determined, and subsequently the deformation field and the inverse deformation field are determined. The transformation matrix is also used for image transformation (together with the inverse deformation field), as only the transformation matrix contains information representative of movements caused by translation or rotation of the patient. Furthermore the transformation matrix, the forward (for continuous point data) and the inverse deformation fields (for volume data) are used for RT structure transformation.

In this embodiment, the deformation field or the inverse deformation field on its own is insufficient for the purpose of object transformation. In other words, at least the transformation matrix and one of the deformation fields is required.

Figure 5:
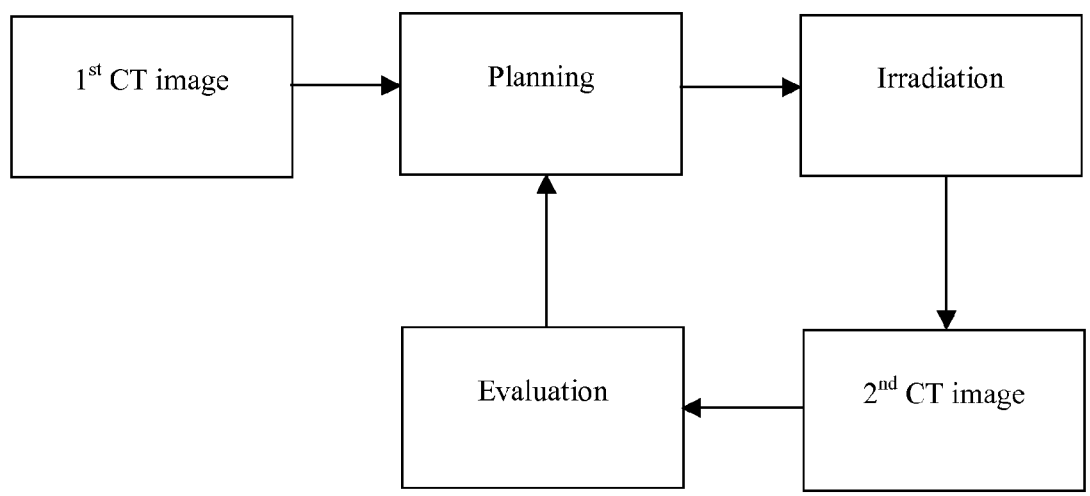
FIG. 5 illustrates a workflow in accordance with an embodiment of the invention.

FIG. 5 illustrates a workflow in accordance with an embodiment of the invention. In a first step, a $1^{st}$ CT image is generated. In a second step, an irradiation planning is performed on the basis of the $1^{st}$ CT image. In a third step, the irradiation is performed. In a fourth step, a second CT image is generated. In a fifth step, the $1^{st}$ and $2^{nd}$ images are processed, as described above.

FURTHER EMBODIMENTS

According to an embodiment there is provided a method comprising: obtaining at least first and second CT images of an object, in particular a patient or a portion thereof; performing a non-rigid registration of the first and second images to determine a deformation field describing a deformation of the object from the first CT image to the second CT image; using the deformation field to determine a transformation of first image portions associated with the first CT image into second image portions associated with the second CT image, wherein the first and second image portions may represent selected contours and/or dosages, in particular contours of organs or irradiation regions and irradiation dosages, respectively; and generating one or more images to visualise the deformation field, wherein the one or more images may be superimposed on the first and/or second CT images.

The method may further comprise processing the deformation field to eliminate a rigid portion thereof attributable to rotation and/or translation of the object.

The method may further comprise generating a transformation matrix describing a transformation of the first CT image into the second CT image; determining said deformation field from the transformation matrix; and additionally using the transformation matrix to determine the transformation of the first image portions associated with the first CT image into the second image portions associated with the second CT image.

The method may further comprise determining an inverse deformation field describing a deformation of the object from the second CT image to the first CT image; and additionally using the inverse deformation field to determine the transformation of the first image portions associated with the first CT image into the second image portions associated with the second CT image.

The method may further comprise making a segmentation of the first and second CT images, thereby generating first and second segmentation images; determining said transformation matrix from the first and second CT images and the first and second segmentation images; and determining said deformation field and said inverse deformation field from the first and second CT images, the first and second segmentation image, and the transformation matrix.

Preferably, the visualisation step comprises generating a colour-coded representation of the absolute value of each of the entries of the deformation field.

Preferably, the deformation field contains 3D vectors, and wherein the step to visualise the deformation field comprises: projecting each of the 3D vectors onto a 2D sectional plane; and generating a colour-coded representation of the projected 2D vectors based on the absolute value of the corresponding 3D vectors.

Preferably, the step to visualise the deformation field comprises displaying a fraction of the 2D vectors selected in accordance with a predetermined selection criterion.

The method may further comprise filtering entries of the deformation field depending on the degree of deformation, in particular entries representative of selected types of deformation such as movements or changes of the object's anatomy.

The method may further comprise filtering entries of the deformation field depending on the size of the region affected by the deformation, in particular entries representative of a deformation that affects a region whose size is not within a predetermined size range.

The method may further comprise iteratively transforming the first image on the basis of filtered entries of the deformation field to obtain a succession of images representing different magnitudes of deformation.

The method may further comprise generating and displaying a histogram of the entries of the deformation field, in particular in respect of a selected region of the object or first or second images.

Preferably, the first image represents an array of 2D polygons, wherein the method comprises: generating a volume from the 2D polygons; transforming the volume; and intersecting the volume with one or more predetermined planes.

It will be appreciated that the above described embodiments are described as examples only, and that modifications to these embodiments are included within the scope of the appended claims.

What is claimed is:

1. A method of evaluating irradiation therapy of a patient, the method comprising:
   obtaining first and second datasets representative of first and second CT images of the patient at different times, respectively;
   obtaining a deformation field, which includes three dimensional vector field entries, representative of changes in one or more regions of the patient between the first and second datasets, wherein the deformation field is generated by performing a rigid or non-rigid registration;
   subsequent to completion of the rigid or non-rigid registration, selectively filtering the entries of the deformation field depending on size of the one or more regions, wherein, for each of the one or more regions whose size is not within a selected size range, the filtering comprises band pass filtering to filter the entries representative of the changes that affect the respective region whose size is not within the selected size range; and
   generating a succession of images representing different magnitudes of deformation based on the first CT image and the filtered entries of the deformation field, thereby to visualize deformations in enabling differentiation between changes in the patient's anatomy and changes, in particular errors, in the patient's position.

2. The method of claim 1, further comprising:
   generating one or more masks and/or segmentations for selecting elements of the first CT image, wherein the selected elements may represent contours, points, and/or dosimetric image portions.

3. The method of claim 1, further comprising visualizing said deformations separately.

4. The method of claim 1, further comprising:
   using algorithms to simultaneously generate forward and backward deformation fields;
   obtaining a rigid transformation attributable to rotation and/or translation of the patient and a non-rigid transformation, attributable to actual deformations inside the patient;
   providing the deformation fields separately and as a combined deformation field; and
   transforming the first dataset using the rigid transformation field and the non-rigid transformation field, or the combined deformation field to project the one or more regions whose size is within the selected size range onto the second CT image.

5. The method of claim 1, further comprising:
   transforming segmentation images with a rigid, non-rigid or combined transformation, for example a deformation field, obtained by a registration from a first image to a second image, wherein the segmentation image is represented by a first set of planar 2D polygons in 3D space;
   generating a 3D volume (3D image matrix) from the set of 2D polygons;
   transforming the volume using predetermined matrix transformation algorithms;
   inserting the volume with planar planes; and
   extracting the contours from the intersected planes to obtain a second set of planar 2D polygons.

6. The method of claim 1, further comprising:
   generating one or more statistical evaluations, in particular histograms, boxplot, mean, variance, of the deformation field or parts of it.

7. The method of claim 1, further comprising:
   visualizing the images as single images or as an image sequence; and
   superimposing resulting images, contours or points on the datasets.

8. The method of claim 1, further comprising:
   generating a forward and a backward/inverse transformation matrix describing a transformation of the first CT image into the second CT image or vice versa;
   determining said deformation field from the transformation matrices; and
   additionally using the transformation matrices to determine the transformation of first image portions associated with the first CT image into second CT image portions associated with the second CT image or vice versa.

9. The method of claim 1, wherein the generating the succession of images comprises generating a colour-coded representation of the absolute value of each of the entries of the deformation field.

10. The method of claim 1, wherein the generating the succession of images comprises:
    projecting each of the entries onto a 2D sectional plane to generate a projected 2D vectors;
    generating a colour-coded representation of the projected 2D vectors based on the absolute value of the corresponding entries;
    generating isocontours based on the magnitude of the projected 2D vectors; and
    displaying the projected 2D vectors with different glyph-types.

11. The method of claim 10, wherein the generating the succession of images comprises displaying a fraction of the projected 2D vectors selected in accordance with a predetermined selection criterion.

12. The method of claim 1, further comprising:
    generating and displaying a histogram of the entries of the deformation field, in particular in respect of the one or more regions of the patient or the first or second CT images.

13. The method of claim 1, wherein the band pass filtering includes filtering to filter the entries representative of the changes that affect the respective region whose size is larger than the selected size range while retaining entries representative of the changes that affect the respective region whose size is within the selected size range.

14. A non-transitory storage medium comprising computer-executable code that, when executed by a computer system, causes the computer system to perform the method of claim 1.

* * * * *